(12) United States Patent
Rhee et al.

(10) Patent No.: US 8,278,051 B2
(45) Date of Patent: *Oct. 2, 2012

(54) METHOD OF AMPLIFYING A TARGET NUCLEIC ACID BY ROLLING CIRCLE AMPLIFICATION

(75) Inventors: Joo-won Rhee, DaeJeon (KR); Young-sun Lee, Yongin-si (KR); Kak Namkoong, Seoul (KR); Chin-sung Park, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/185,003

(22) Filed: Jul. 18, 2011

(65) Prior Publication Data

US 2011/0269193 A1    Nov. 3, 2011

Related U.S. Application Data

(63) Continuation of application No. 12/247,433, filed on Oct. 8, 2008, now Pat. No. 8,003,322.

(30) Foreign Application Priority Data

Oct. 11, 2007 (KR) .......................... 10-2007-0102581

(51) Int. Cl.
*C12Q 1/68* (2006.01)
*C12P 19/34* (2006.01)

(52) U.S. Cl. ...................................... 435/6.12; 435/91.2

(58) Field of Classification Search .................. 435/6.12, 435/91.2

See application file for complete search history.

(56) References Cited

U.S. PATENT DOCUMENTS

| | | | |
|---|---|---|---|
| 6,235,502 B1 | 5/2001 | Weissman et al. | |
| 6,498,023 B1 | 12/2002 | Abarzua | |
| 8,003,322 B2 * | 8/2011 | Rhee et al. ................... | 435/6.12 |
| 2001/0039039 A1 | 8/2001 | Weissman et al. | |
| 2004/0029235 A1 | 2/2004 | Atkinson et al. | |
| 2005/0069939 A1 | 3/2005 | Wang et al. | |
| 2007/0015182 A1 | 1/2007 | Abarzua | |
| 2007/0031857 A1 | 2/2007 | Makarov et al. | |

FOREIGN PATENT DOCUMENTS

| | | |
|---|---|---|
| KR | 1020060073815 A | 6/2006 |
| WO | 2006119066 A2 | 11/2006 |
| WO | 2007/018601 A1 | 2/2007 |

OTHER PUBLICATIONS

Alsamadi et al. "High Accuracy Genotyping Directly from Genomic DNA using a Rolling Circle Amplification Based Assay." BMC Genomics, BIOMED Central, Great Britian vol. 4, No. 1, May 2003, pp. 1-18.
Fire et al., "Rolling replication of short DNA circles," Proc. Natl. Acad. Sci. USA, vol. 92, pp. 4641-4645, May 1995.
Demidov, "Rolling-circle amplification in DNA diagnostics: the power of simplicity," Expert Rev. Mol. Diagn. 2(6), 2002.

* cited by examiner

*Primary Examiner* — Kenneth R. Horlick
*Assistant Examiner* — Joyce Tung
(74) *Attorney, Agent, or Firm* — Sughrue Mion, PLLC (57) ABSTRACT

Provided is a method of amplifying a nucleic acid using rolling cyclic amplification (RCA), including amplifying a nucleic acid together with formation of a single-strand circular DNA template using RCA by reacting a reaction solution including: (a) two hairpin oligos, (b) a target nucleic acid, (c) a DNA ligase, (d) an endonuclease, (e) a DNA polymerase, and (f) a primer.

22 Claims, 6 Drawing Sheets

5'-NNNGAATTCNN-3'　　LIGASE AND EcoRI　　5'-NNNG-3'　　5'-AATTCNN-3'
3'-NNNCTTAAGNN-5'　　⟷　　　　　　　　　3'-NNNCTTAA-5'　　3'-GNN-5'
　　　T　　　　　　　　　　　　　　　　　　　　T1　　　　　　　　T2

(B)

A　5'-NNTTTAA-3'　　　　　　　　　　　　　　5'-NNNGAATTTNN-3'　H
　　3'-NNA-5'　　　　　　　　　　　　　　　　3'-NNNCTTAAANN-5'
　　　+　　　　　LIGASE AND EcoRI　　　　　　　+
　　　　　　　　　⟷
T　5'-NNNGAATTCNN-3'　　　　　　　　　　　5'-NNNGAATTCNN-3'　T
　　3'-NNNCTTAAGNN-5'　　　　　　　　　　　3'-NNNCTTAAGNN-5'

SEQUENCE LISTING

<160> NUMBER OF SEQ ID NOS: 5

<210> SEQ ID NO 1
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 1
ccgacgagcg agctttaacg tgcgctaact gcggtcagaa gctgcatgtg tc        52

<210> SEQ ID NO 2
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 2
ccattctgtt ccgcatgatt cctctgcgga acagaat                         37

<210> SEQ ID NO 3
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 3
ggattctgtt ccgcatgatt cctctgcgga acagaat                         37

<210> SEQ ID NO 4
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 4
cgacgagcga gctttaacgt g                                          21

<210> SEQ ID NO 5
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 5
gcggaacaga atgggacac                                             19

METHOD OF AMPLIFYING A TARGET NUCLEIC ACID BY ROLLING CIRCLE AMPLIFICATION

CROSS-REFERENCE TO RELATED PATENT APPLICATIONS

This is a continuation application of U.S. application Ser. No. 12/247,433, which claims the benefit of Korean Patent Application No. 10-2007-0102581, filed on Oct. 11, 2007, in the Korean Intellectual Property Office, the disclosure of which is incorporated herein in its entirety by reference.

BACKGROUND OF THE INVENTION

1. Field of the Invention

The present invention relates to a kit for and a method of amplifying a target nucleic acid using rolling circle amplification (RCA) method in the presence of a ligase and a restriction enzyme.

2. Description of the Related Art

In rolling circle amplification (RCA) method, a polymerization reaction is carried out at a temperature, for example, at room temperature, using a single-stranded (or "single-strand") circular DNA as a template and a primer which is complementary to the single-strand circular DNA, to synthesize multiple continuous single-stranded linear copies of the template DNA. The RCA method has a high degree of sensitivity and thus has been successfully used for amplification of DNA from small amounts of starting material, but it is difficult to prepare a single-strand circular DNA template itself. A single-strand circular DNA can be chemically synthesized or prepared through a separate reaction.

U.S. Pat. No. 5,714,320 discloses a method of synthesizing a selected oligonucleotide having well-defined ends, which include steps: (a) annealing an effective amount of an oligonucleotide primer to a single-strand circular template to yield a primed circular template, wherein the single-strand circular template includes (i) at least one copy of a nucleotide sequence complementary to the sequence of the selected oligonucleotide and (ii) at least one nucleotide effective to produce a cleavage site in the oligonucleotide multimer; (b) combining the primed circular template with an effective amount of at least two types of nucleotide triphosphates and an effective amount of a polymerase enzyme without the addition of auxiliary proteins to yield a single-strand oligonucleotide multimer complementary to the circular oligonucleotide template, wherein the oligonucleotide multimer includes multiple copies of the selected oligonucleotide; and (c) cleaving the oligonucleotide multimer at the cleavage site to produce the selected oligonucleotide having well-defined ends. Also, Proc. Natl. Acad. Sci. USA, Vol. 92, pp. 4641-4645 (May in 1995) discloses that RCA is used to amplify a DNA circle as short as 34 bp.

However, synthesis of the single-strand circular DNA template and amplification of a target nucleic acid have not been performed in the same vessel. In addition, a method of performing RCA in the presence of both a ligase and an endonuclease has not been disclosed.

SUMMARY OF THE INVENTION

The present invention provides a method of amplifying a single-strand circular DNA template and a target nucleic acid in a single reaction vessel using rolling circle amplification (RCA).

According to an aspect of the present invention, there is provided a method of amplifying a nucleic acid using RCA, in which the method includes amplifying a nucleic acid together with formation of a single-strand circular DNA template using RCA by allowing a solution including: (a) a first hairpin oligonucleotide which comprises a loop region, a double-stranded region, and a single-stranded end sequence ("first overhang sequence"), (b) a second hairpin oligonucleotide which comprises a loop region, a double stranded region, and a single-stranded end sequence ("second overhang sequence") at its 5' or 3' end, wherein the overhang sequence of the second hairpin oligonucleotide is complementary to the overhang sequence of the first hairpin oligonucleotide, (c) a target nucleic acid having a single-stranded end sequence complementary to the first or second overhang sequence of the first or second hairpin oligonucleotides, (d) a DNA ligase, (e) an endonuclease, (f) a DNA polymerase, and (g) a primer oligonucleotide, to react in a single reaction solution.

According to a further aspect of the invention, there is provided a kit for the amplification of a target nucleic acid molecule according to the method of the present application, comprising (a) a first hairpin oligonucleotide which comprises a first loop region, a first double-stranded linear region, and a first single-stranded end sequence ("first overhang sequence"), (b) a second hairpin oligonucleotide which comprises a second loop region, a second double stranded linear region, and a second single-stranded end sequence ("second overhang sequence"), wherein the second overhang sequence of the second hairpin oligonulceotide is complementary to the first overhang sequence of the first hairpin oligonucletodie, (c) the target nucleic acid molecule having a single-stranded end sequence complementary to the first or second overhang sequence; (d) a DNA ligase; and (e) an endonuclease. Preferably, the kit further comprises (f) a DNA polymerase; and (g) a primer oligonucleotide.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

In the present specification, the term "oligonucleotide" is sometimes referred to as "oligo" for convenience. The "oligo" or "oligonucleotide" is comprised of from about 5 nucleotides to about 100 nucleotides. In one embodiment, the "hairpin oligonucleotide" is comprised of about 10 to about 30 nucleotides.

A method of amplifying a target nucleic acid according to the present invention is performed with rolling circle amplification (RCA) using a DNA polymerase in the presence of ligase and endonuclease which has an opposite activity to the ligase in a single reaction solution. As a result of such reaction, two oligos can be ligated to each other by the ligase to form a hairpin dimer, a single hairpin oligo can be ligated to a target nucleic acid molecule, a target nucleic acid molecule can be ligated to another target nucleic acid in a head-to-tail manner to form a concatemer, and two hairpin oligos can be ligated to a target nucleic acid molecule to form a single-strand circular DNA molecule. Herein, the single-strand circular DNA can act as a template in a RCA reaction. As described above, a product formed by a ligase can be cleaved by an endonuclease. Therefore, when a ligase and an endonuclease co-exist in a reaction solution, a product formed by the ligase ("ligation product") and another product obtained by cleaving the ligation product using the endonuclease ("nuclease lysis product") co-exist in an equilibrium state. The method of amplifying a nucleic acid using RCA according to the present invention includes performing RCA using a single-strand circular DNA, as a template, which exits in such equilibrium state.

In such equilibrium state, the formation of the single-strand circular DNA molecule can be achieved using various methods. For example, the formation of a single-strand circular DNA molecule by joining the target nucleic acid to the two hairpin oligos (i.e., the 3' end of the target nucleic acid is joined to the 5' end of first hairpin oligo and the 5' end of the target nucleic acid is joined to the 3' end of second hairpin oligo, or vice versa) can be facilitated by designing the hairpin oliogs in such a way that the ligated product of the two hairpin oligos and the target nucleic acid does not have an endonuclease recognition site in a double-strand linear segment (also known as a "stem region" in the art). Also, more single-strand circular DNA can be obtained by maintaining the concentration of the hairpin oligo higher than the concentration of the target nucleic acid.

The terminology "hairpin oligo" or "hairpin oligonucleotide" used in the method of amplifying a nucleic acid molecule according to the present invention is a molecule which has a segment (also known as a "hairpin loop") that is not hybridized with or complementary to a segment of the same hairpin oligo, and a double-stranded linear segment (also known as a "stem") consisting of segments that are complementary to each other in the same molecule. The hairpin oligo can be referred to as a stem and loop structure in a field related to a nucleic acid manipulation.

In the present invention, the hairpin oligos may be comprised of 15-200 nucleotides, for example, 37 nucleotides. The loop region may have 5-50 nucleotides, for example, 9 nucleotides, and the overhang sequence may have 2-8 nucleotides, for example, 4 nucleotides. However, the length of the hairpin oligos, loop region and overhang sequence, is not limited to the above exemplified length.

In the method of amplifying a nucleic acid molecule according to the present invention, the two hairpin oligos can be ligated to each other by the ligase to form a monomer which has a single-strand hairpin loop at its ends and a double-strand linear segment having an endonuclease (e) restriction site. Even when two hairpin oligos are linked to each other without a target nucleic acid to form a hairpin dimer, the hairpin dimer can be cleaved by the endonuclease. Therefore, the concentration of the hairpin dimer can be reduced.

Figure 2:
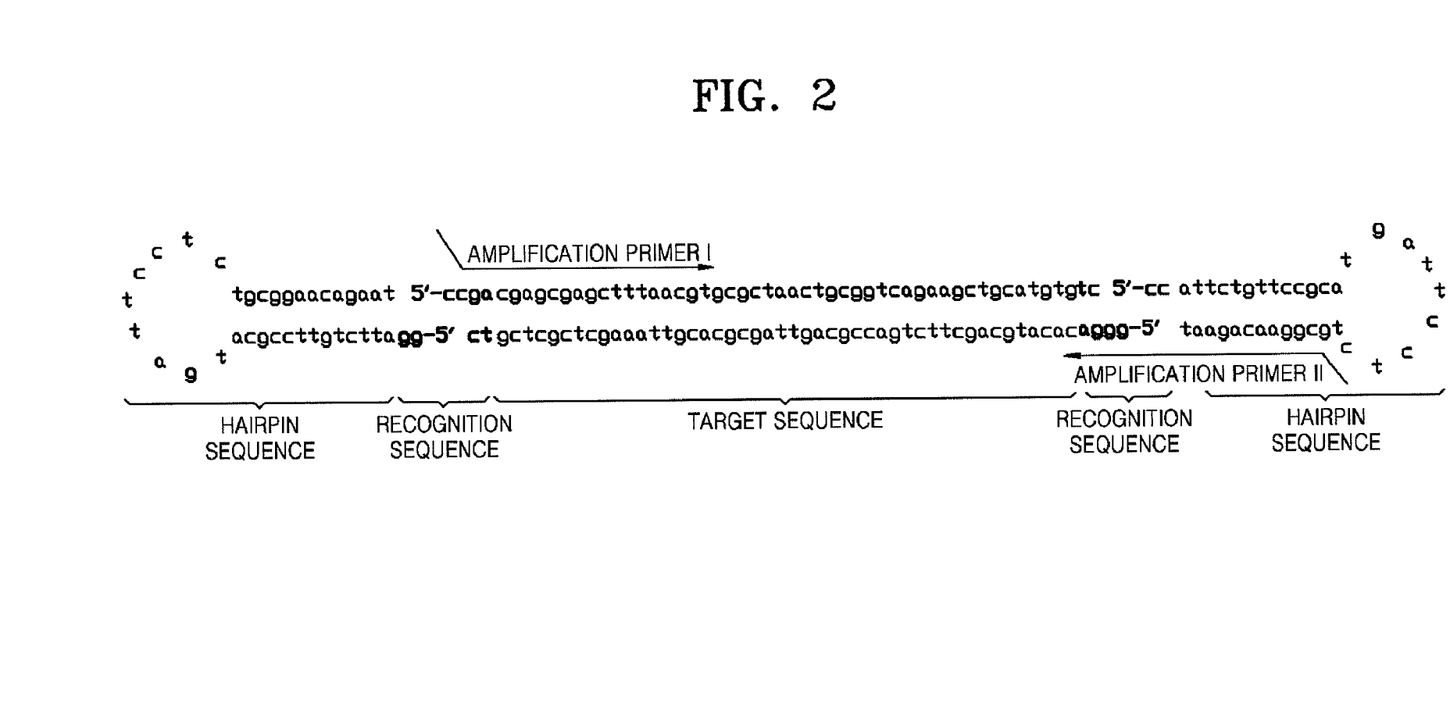
FIG. 2 illustrates a monomer in which a target nucleic acid is linked to and between two hairpin oligonucleotides.

In the method of amplifying a nucleic acid according to the present invention, the two hairpin oligos can be linked to a target nucleic acid by the ligase to form a monomer which has a single-strand hairpin loop at its ends and has a double-strand linear segment, as exemplified in FIG. 2. The double-strand linear segment may or may not have an endonuclease (e) restriction site. In an embodiment, the double-strand linear segment of the monomer formed by linking the two hairpin oligos to a target nucleic acid such that the target nucleic acid is ligated to one of the two hairpin oligos at '5 end and to the other of the two hairpin oligos at 3' end and does not generate a recognition site for the (e) endonuclease around its ligation sites. For example, when the (e) endonuclease is an EcoRI enzyme having a recognition site of GAATTC, and a . . . AT single-strand end may be formed in the target nucleic acid through the operation of the EcoRI enzyme. In this regard, a single-strand end of the hairpin oligo has TA . . . sequence which is complementary to a sequence of . . . AT and nucleotides which follow TA have a different sequence from a recognition site sequence for EcoRI. As a result, the double-strand linear segment of the monomer formed by ligating the two hairpin oligos to a target nucleic acid such that the target nucleic acid is placed between two hairpin oligos may not have the recognition site for EcoRI. Such combinations can be carried out without undue difficulties by one of ordinary skill in the art using a restriction enzyme and a recognition site thereof.

A target nucleic acid used in the present invention has a single-strand end sequence complementary to the single-strand end sequence of at least one of the two hairpin oligos. The target nucleic acid can be prepared in advance, or can be prepared in situ from a sample nucleic acid in a sample in a reaction solution by the (e) endonuclease. For example, a genome DNA solution that is a sample can be added to a reaction solution and the DNA can be cleaved by the (e) endonuclease to obtain the target nucleic acid in situ. The target nucleic acid can be a double stranded nucleic acid molecule having a single stranded end sequence ("overhang sequence") or single stranded nucleic acid. In either case, the overhang sequence of the double-stranded molecule and the 2-5 nucleotides end sequence of the singed-stranded molecule are each complementary to the overhang sequence of at least of the two hairpin oligos. The target nucleic acid sequence may have 256-4096 base pairs (bp). However, the length of the target nucleic acid is not limited to the above exemplified length.

In the method of amplifying a nucleic acid according to the present invention, the reaction can be carried out using a ligase, a DNA polymerase, and a restriction enzyme buffer which are commercially available. In this regard, ATP which is specifically required for a ligase reaction, restriction enzyme, $Mg^{2+}$ which is specifically required for a restriction enzyme reaction, and dNTP which is specifically required for a polymerase reaction should be used in the reaction. Examples of the restriction enzyme buffer include New England Biolab (NEB)™ buffer series which are commonly used in a restriction enzyme reaction. For example, such restriction enzyme buffer can be NEB buffer 4, Bst DNA polymerase buffer, or T4 DNA ligase buffer. However, the restriction enzyme buffer is not limited to these buffers.

The reaction can be performed at a temperature in the range of 4° C. to 80° C., preferably 4° C. to 65° C.

The reaction can be performed at a pH of 5 to 9, preferably 6 to 7.5.

The reaction can be performed in a reaction solution including $Mg^{2+}$, dNTP, and ATP.

In the method of amplifying a nucleic acid according to the present invention, the ligase can be selected from the group consisting of a Taq DNA ligase, *E. coli* DNA ligase, T4 DNA ligase, and Tfi DNA ligase.

In the method of amplifying a nucleic acid according to the present invention, the endonuclease can be selected from the group consisting of type-I, II, IIs, Iig, IIb, nicking endonuclease, McrBC nuclease, and a homing nuclease.

The molar ratio between the ligase and the endonuclease may be in the range from 0.1-10:1. In one embodiment, the ratio is about 1:1.

In the method of amplifying a nucleic acid according to the present invention, the DNA polymerase can be selected from the group consisting of *E. coli* DNA polymerase I, Klenow fragment, phi29 DNA polymerase, vent DNA polymerase, T4, T7 DNA polymerase, and Taq polymerase.

In the method of amplifying a nucleic acid according to the present invention, the primer can be complementary to one or more elements selected from the group consisting of a target nucleic acid and two hairpin oligos. Specifically, the primer can have, in addition to a sequence complementary to a target nucleic acid, a sequence complementary to a hairpin oligo so that amplification of a hairpin dimer can be prevented and the primer can more specifically amplify the target nucleic acid.

The primer may consist of two primers so that the target nucleic acid can be amplified into an individual target nucleic acid unit, not into a plurality of concatemers.

According to an embodiment of the kit, the first overhang sequence of the first hairpin oligonucleotide and the second overhang sequence of the second hairpin oligonucleotide have a nucleotide sequence which generates a restriction site for the (e) endonuclease in a double stranded linear region which is formed by ligation of the first hairpin oligonucleotide and the second hairpin oligonucleotide.

According to a further embodiment of the kit, the target nucleic acid molecule is double stranded and each strand of the two strands of the target nucleic acid has a single stranded end sequence at its one end; and wherein the single stranded end sequence of one strand is complementary to the first overhang sequence of the first hairpin oligonucleotide and the single stranded end sequence of the other strand is complementary to the second overhang sequence of the second hairpin oligonucleotide.

According to a further embodiment of the kit, the target nucleic acid molecule is double stranded and one of the two strands of the target nucleic acid has a single stranded end sequence at its both ends; and wherein the single stranded end sequence of one end is complementary to the first overhang sequence of the first hairpin oligonucleotide and the single stranded end sequence of the other end is complementary to the second overhang sequence of the second hairpin oligonucleotide.

According to a further embodiment of the kit, the target nucleic acid molecule is double stranded and has a single stranded end sequence at one end; and wherein the single stranded end sequence of the target nucleic acid molecule is complementary to one of the first overhang sequence of the first hairpin oligonucleotide or the second overhang sequence of the second hairpin oligonucleotide.

According to a further embodiment of the kit, the target nucleic acid molecule is ligated, at its one end, to the first hairpin oligonucleotide and, at its other end, to the second hairpin oligonucleotdie to form a monomer which has a single-strand hairpin loop at its both ends and has a double stranded linear region. Preferably, the double stranded linear region has or does not have a restriction site for the (e) endonuclease.

According to a further embodiment of the kit, the primer oligonucleotide is complementary to the target nucleic acid molecule and/or to the double stranded linear region of the first or the second hairpin oligonucleotides. Preferably, the primer oligonucleotide comprises two primer oligonucleotides.

An operational principle of the method of amplifying a nucleic acid according to the present invention will now be described in detail with reference to FIGS. 1 and 2.

Figure 1:
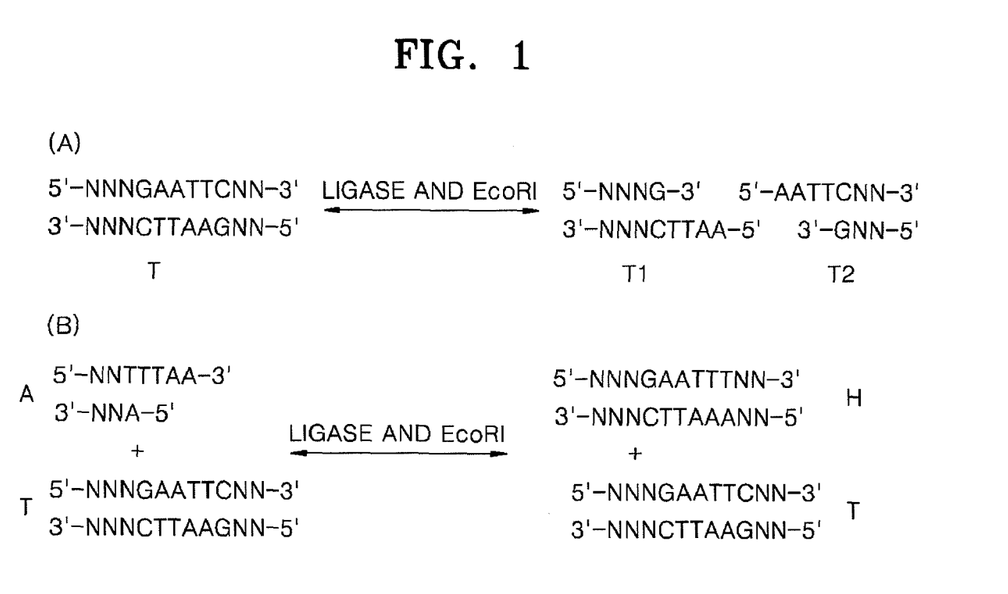
FIG. 1 illustrates an equilibrium state of a reaction solution in which a ligase and a restriction endonuclease EcoRI coexist.

FIG. 1 illustrates an equilibrium state of a reaction solution in which a ligase and a restriction endonuclease EcoRI co-exist. In FIG. 1, (A) illustrates an equilibrium state of a reaction solution which contains a nucleic acid T which has a EcoRI recognition site alone, and (B) illustrates an equilibrium state of a reaction solution which contains a nucleic acid T having a EcoRI recognition site as well as a nucleic acid A (hereinafter referred to as adaptor nucleic acid) having a sequence complementary to a sticky end (i.e., single-strand end sequence) formed by cleavage of EcoRI. Referring to FIG. 1, it can be seen that, in a solution including a ligase and a restriction endonuclease, the addition of an adaptor nucleic acid A, in addition to the nucleic acid T having an endonuclease recognition site, leads to the formation of the hybrid nucleic acid H (T1-A hybrid). The two hairpin oligos described above may be the adaptor nucleic acid in FIG. 1, and the target nucleic acid may be the nucleic acid T having an endonuclease recognition in FIG. 1. These two hairpin oligos and a hairpin dimer formed by joining the two hairpin oligos can exist in an equilibrium state in a reaction solution in which a ligase and a restriction endonuclease co-exist. Therefore, according to the present invention, the two hairpin oligos can be exchangeable with a hairpin dimer formed by ligation of the two oligos in a reaction solution, which should be considered to fall in the scope of the invention. In FIG. 1, a recognition site GAATTC for EcoRI in the nucleic acid T is not formed in a hybrid nucleic acid H. Therefore, more hybrids are formed than the nucleic acid T or the adapter nucleic acid A, and thus, even when the concentration of the nucleic acid T is low, a single-strand circular DNA template, that is, a hybrid nucleic acid H can be obtained.

FIG. 2 illustrates a monomer in which a target nucleic acid is ligated to and between two hairpin oligos. Referring to FIG. 2, a target nucleic acid consisting of ccgacgagcgagctttaacgtgcgctaactgcggtcagaagctgcatgtgtc (SEQ ID NO: 1) is ligated at its 3' end to a first hairpin oligo consisting of ccattctgttccgca tgattcctctgcggaacagaat (SEQ ID NO: 2), and at its 5' end to a second hairpin oligo consisting of ggattctgttccgcatgattcctct-gcggaacagaat (SEQ ID NO: 3) by the action of a ligase. The target nucleic acid illustrated in FIG. 2 is double stranded, and each strand has a 5' end overhang sequence, which is complementary to the overhang sequence of the first or second hairpin oligo. Also, the overhang sequences of the first and second hairpin oligos are complementary to each other. However, ends of the target nucleic acid can have the same single-strand end sequence which is complementary to the overhang sequence of only one of the first and second hairpin oligos. Also, one of the two strands of the target nucleic acid may have overhang sequences at both ends, which each may be complementary to the overhang sequence of one of the hairpin oligos, or to the overhang sequence of respective hairpin oligos. In FIG. 2, the recognition site for the restriction enzyme is tccc, and the binding sites of primers I and II are shown. The primer I has a sequence of cgacgagcgagctttaacgtg (SEQ ID NO: 4) and the primer II has a sequence of gcggaacagaatgggacac (SEQ ID NO: 5). Specifically, the primer II is complementary to the overhang sequence of the hairpin oligos and the target nucleic acid.

According to the method of amplifying a nucleic acid according to the present invention, formation of a single-strand circular DNA template and RCA can be concurrently performed in a single reaction vessel. In addition, the method enables amplification of a double-strand DNA which is difficult to be amplified by conventional isothermal amplification. The method of amplifying a nucleic acid according to the present invention uses a target DNA itself as an amplification core, that is, a dumbbell, to perform amplification, and thus, a degree of amplification specificity is high. Furthermore, the method of amplifying a nucleic acid according to the present invention can also be applied to SNP typing by changing a different restriction enzyme. Also, the method may use a type IIs restriction enzyme and a primer complementary to a loop of a hairpin oligo so that the entire genome can be amplified.

The present invention will be described in further detail with reference to the following examples. These examples are for illustrative purposes only and are not intended to limit the scope of the present invention.

Experimental Example 1

Compatibility of Restriction Enzyme Buffer and DNA Polymerization Buffer

The current Experimental Example was performed to identify that a buffer used for a restriction enzyme reaction can be compatible with respect to a buffer used for DNA polymerization.

1500 ng of Lambda DNA (Bioneer, Korea) was added to 10 µl of NEB buffer 4 (consisting of 50 mM potassium acetate, 20 mM Tris-acetate, 10 mM magnesium acetate, and 1 mM dithiothreitol, pH 7.9 at 25° C.), and 3 units of Hpy188III were added thereto. The obtained solution was reacted at room temperature for 10 minutes (use of restriction enzyme buffer). Hpy 188III had a recognition site of TCNNGA, and is a type IIs. In addition, 1500 ng of Lambda DNA (Bioneer, Korea) was added to 10 µl of $Mg^{2+}$ and ATP-added Bst DNA polymerase buffer [1×Bst buffer (20 mM Tris-HCl, 10 mM $(NH_4)_2SO_4$, 10 mM KCl, 2 mM $MgSO_4$, 0.1% Triton X-100, pH 8.8 at 25° C.), 7.5 mM $Mg^{2+}$, 0.6 µM of each primer (SEQ ID NO: 4 and 5), 0.3 mM dNTP each, 5 units of Bst DNA polymerase, 1 mM ATP, and SYBR 2X], and 3 units of Hpy188III was added thereto. The obtained solution was reacted at room temperature for 10 minutes (use of DNA polymerization enzyme buffer). As a control group, 1500 ng of Lambda DNA was reacted in 10 µl of NEB buffer 4 without addition of Hpy188III.

Figure 3:
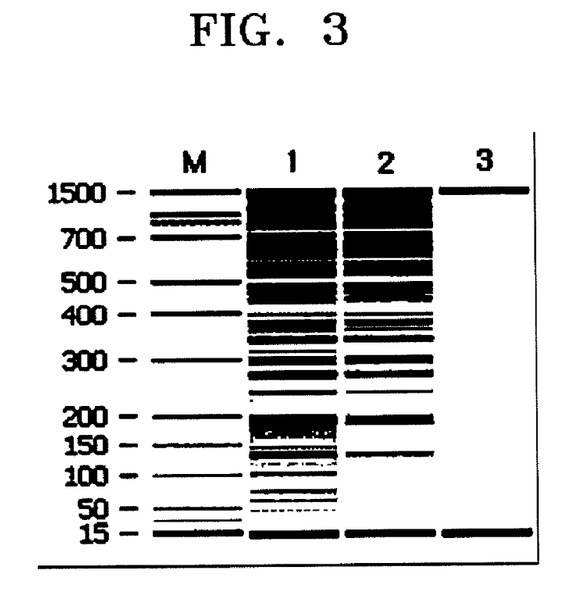
FIG. 3 illustrates a mutual compatibility of a restriction enzyme buffer and a polymerization enzyme buffer.

The reaction product was analyzed using Labchip™ (Agilent Technology). The results are shown in FIG. 3. FIG. 3 illustrates a mutual compatibility of a restriction enzyme buffer and a polymerization enzyme buffer. In FIG. 3, M shows a marker band, Lane 1 shows results of NEB buffer 4, Lane 2 shows results of Bst DNA polymerase buffer, and Lane 3 shows results of a negative control group. As shown in Lanes 1 and 2, cleaved products showed similar results. Therefore, it can be seen that a polymerization enzyme buffer does not affect reaction of a restriction enzyme.

Experimental Example 2

Compatibility of DNA Buffer and Ligase Buffer

The current Experimental Example was performed to identify that a buffer used for a DNA polymerization reaction can be compatible with respect to a ligase buffer.

1500 ng of Lambda DNA (Bioneer, Korea) was added to 10 µl of T4 DNA ligase buffer (consisting of 50 mM Tris-HCl, 10 mM $MgCl_2$, 1 mM ATP, 10 mM Dithiothreitol, pH 7.5 at 25° C.), and 3 units of Hpy188III and 3 units of T4 DNA ligase were added thereto. The obtained solution was reacted at room temperature for 20 minutes (use of ligase buffer). Also, 1500 ng of Lambda DNA (Bioneer, Korea) was added to 10 µl of $Mg^{2+}$ and ATP-added Bst DNA polymerase buffer [1×Bst buffer (20 mM Tris-HCl, 10 mM $(NH_4)_2SO_4$, 10 mM KCl, 2 mM $MgSO_4$, 0.1% Triton X-100, pH 8.8 at 25° C.), 7.5 mM $Mg^{2+}$, 0.6 µM each primer, dNTP 0.3 mM each, Bst DNA polymerase 5 unit, 1 mM ATP, SYBR 2X], and 3 units of Hpy188III and 3 units of T4 DNA ligase were added thereto. The obtained solution was reacted at room temperature for 20 minutes (use of DNA polymerization enzyme buffer). As a control group, the same reaction was carried out in the same manner as in the ligase buffer, except that the T4 DNA ligase was not used. Primers had SEQ ID NOS. 4 and 5.

Figure 4:
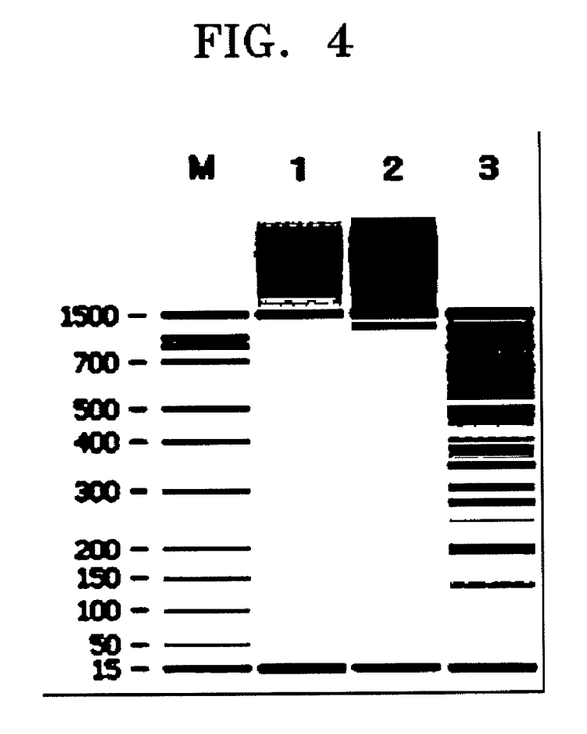
FIG. 4 illustrates a mutual compatibility of a ligase buffer, a restriction enzyme, and a polymerization enzyme buffer.

The reaction product was analyzed using Labchip™ (Agilent Technology). The results are shown in FIG. 4. FIG. 4 illustrates a mutual compatibility of a ligase buffer, a restriction enzyme, and a polymerization enzyme buffer. Referring to FIG. 4, M shows a marker band, Lane 1 shows results of the ligase buffer, Lane 2 shows results of the Bst DNA polymerase buffer, and Lane 3 shows results of the same experiment as in Lane 1, except that the T4 DNA ligase was not used. As shown in Lanes 1 and 2, there is no difference between cleaved products. Therefore, it can be seen that the polymerization enzyme buffer does not affect the reaction of the ligase.

Experimental Example 3

Equilibrium State of Product in Solution in which Ligase and Restriction Enzyme Co-Exist The current Experimental Example was performed to identify a change in an equilibrium state of a product when a solution including a target nucleic acid and two hairpin oligos is treated with a ligase, with a restriction enzyme, and with both the ligase and the restriction enzyme.

20 µl of a reaction solution included 0.5 µM target DNA (SEQ ID NO: 1), 5 µM each hairpin oligo (SEQ ID NOS: 2 and 3), 1×Bst buffer (20 mM Tris-HCl, 10 mM $(NH_4)_2SO_4$, 10 mM KCl, 2 mM $MgSO_4$, 0.1% Triton X-100, pH 8.8 at 25° C.), 7.5 mM $Mg^{2+}$, 0.6 µM each primer (SEQ ID NO: 4 or 5), 0.3 mM dNTP each, 5 units of Bst DNA polymerase, 1 mM ATP, and SYBR 2X. 3 units of T4 DNA ligase (Lane 1) and 3 units of T4 DNA ligase and 3 units of a restriction enzyme Hpy188III were added thereto in a ratio of 1:1 (Lane 2), 3 units of a restriction enzyme Hpy188III (Lane 3) were added thereto. The obtained solution was reacted at room temperature for 10 minutes. The reaction product was analyzed using Labchip™ (Agilent Technology). The results are shown in FIG. 5.

Figure 5:
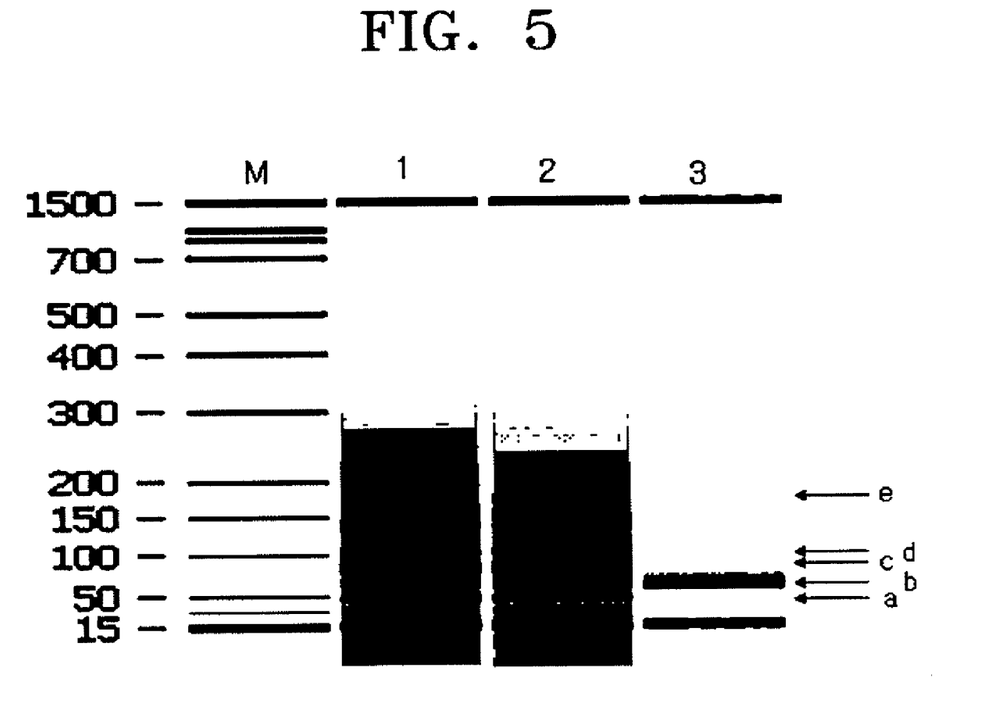
FIG. 5 illustrates results of an experiment performed to identify that a restriction enzyme is active in a polymerization enzyme buffer in the presence of a target nucleic acid and two hairpin oligonucleotides.

FIG. 5 illustrates results of identification showing that a restriction enzyme is active in a polymerization enzyme buffer in the presence of a target nucleic acid and two hairpin oligos. Referring to FIG. 5, M shows a marker band, Lane 1 shows results when only ligase was added, Lane 2 shows results when ligase and restriction enzyme were added in a ratio of 1:1, and Lane 3 shows results when only a restriction enzyme was added. As shown in Lanes 1 and 2, when ligase and restriction enzyme were added in a ratio of 1:1 (Lane 2), a monomer in which a target nucleic acid is ligated to and between two hairpin oligos (such monomer is also called as a "dumbbell") is increased by 32%, a target nucleic acid and a concatemer thereof were reduced by 66%, and a hairpin dimer was reduced by 32%, compared when only ligase was added (Lane 1). Therefore, it can be seen that the co-presence of the ligase and the restriction enzyme in a reaction solution leads to a substantial increase of a monomer in which a target nucleic acid is ligated to and between two hairpin oligos, that is, a substantial increase of DNA to be used as a template in RCA. In FIG. 5, the band of a hairpin dimer is located at a, the band of a single target DNA is located at b, the band of a product obtained by ligating a single hairpin oligo to a single target nucleic acid is located at c, the band of a monomer in which a target nucleic acid is ligated to and between two hairpin oligos is located at d, and the band of a target nucleic acid concatemer is located at e. The band of a product obtained by ligating a single hairpin oligo to a single target nucleic acid located at c may be formed because phosphorylation of 5' end of the hairpin oligo may not be carried out in the yield of 100%.

Example 1

RCA in the Presence of Ligase and Restriction Enzyme

RCA was performed after identifying that a single-strand circular DNA acting as a template in RCA was amplified in a great quantity in the presence of both a ligase and a restriction enzyme according to results of Experimental Examples 1-3.

20 μl of reaction solution included 0.5 pM target DNA (SEQ ID NO: 1), 0.5 pM hairpin oligo (SEQ ID NOS: 2 and 3), 1×Bst buffer (20 mM Tris-HCl, 10 mM $(NH_4)_2SO_4$, 10 mM KCl, 2 mM $MgSO_4$, 0.1% Triton X-100, pH 8.8 at 25° C.), 7.5 mM $Mg^{2+}$, 0.6 μM of each primer (SEQ ID NO: 4 or 5), 0.3 mM dNTP each, 5 units of Bst DNA polymerase, 1 mM of ATP, and SYBR 2X. When only 3 units of a ligase were added to the reaction solution (positive control group), when only 3 units of a restriction enzyme were added (negative control group), and when 3 units of a ligase and 3 units of a restriction enzyme were added, a isothermal amplification, that is, RCA was performed. That is, the reaction solution was loaded to a TMC-1000™ thermal cycler (Samsung Electronics, Co. Ltd) and left to sit at room temperature for 10 minutes. Then, the RCA was performed by repeating 40 times for 5 seconds at 60° C. and 40 seconds at 60° C. (that is, for 45 seconds at 60° C.; such division of 5 seconds and 40 seconds is due to the fact that a TMC-1000™ device is set in a form of thermal cycle). Intensity of fluorescence was measured for the final 5 seconds of each cycle.

Figure 6:
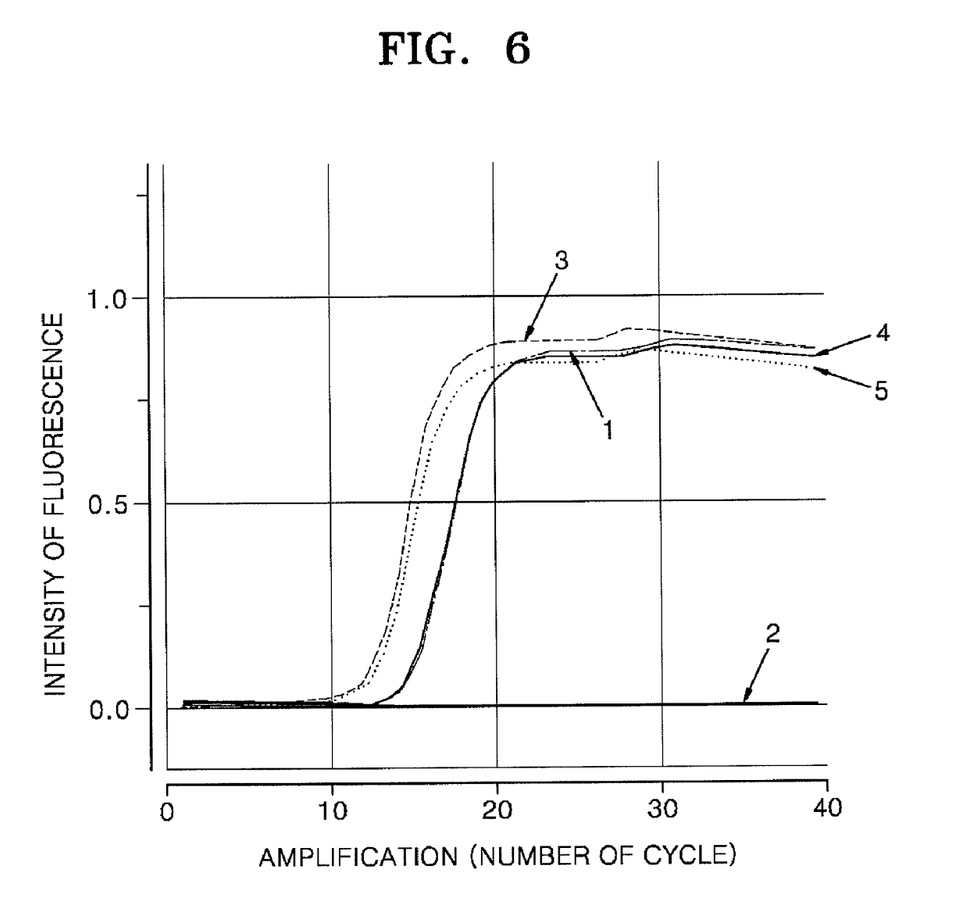
FIG. 6 illustrates results of RCA performed in the presence of a ligase and a restriction enzyme.

FIG. 6 illustrates results of RCA performed in the presence of a ligase and a restriction enzyme. Referring to FIG. 6, curves 1 and 4 (twice in each experiments) were obtained when RCA was performed in the presence of a ligase alone, curve 2 was obtained when RCA was performed in the presence of a restriction enzyme alone (although there is only one curve in FIG. 6, in fact, two curves obtained from two experiments overlap), and curves 3 and 5 (two experiments) were obtained when RCA was performed in the presence of a ligase and a restriction enzyme in the mixture ratio of 1:1. Referring to FIG. 6, when RCA was performed in a solution containing a ligase and a restriction enzyme, the target nucleic acid was quickly amplified.

Example 2

RCA in the Presence of Ligase and Restriction Enzyme—Effect on Sensitiveness

RCA was performed in the presence of a ligase and a restriction enzyme while the concentration of a target nucleic acid was varied.

20 μl of a reaction solution included a target DNA (SEQ ID NO: 1) having a concentration of 106 to 10 copy, 0.5 pM hairpin oligos (SEQ ID NOS: 2 and 3), 1×Bst buffer (20 mM Tris-HCl, 10 mM $(NH_4)_2SO_4$, 10 mM KCl, 2 mM $MgSO_4$, 0.1% Triton X-100, pH 8.8 at 25° C.), 7.5 mM $Mg^{2+}$, 0.6 μM each primer (SEQ ID NO: 4 or 5), 0.3 mM dNTP each, 5 units of Bst DNA polymerase, 1 mM of ATP, and SYBR 2X. 3 units of T4 DNA ligase and 3 units of Hpy188III restriction enzyme were added to the reaction solution, and then an isothermal amplification, that is, RCA was performed. That is, the reaction solution was loaded to a TMC-1000™ thermal cycler (Samsung Electronics, Co. Ltd) and was left to sit at room temperature for 10 minutes. Then, the RCA was performed by repeating 40 times for 5 seconds at 60° C. and 40 seconds at 60° C. (that is, for 45 seconds at 60° C.; such division of 5 seconds and 40 seconds is due to the fact that a TMC-1000™ device is set in a form of thermal cycle). Intensity of fluorescence was measured for the final 5 seconds of each cycle.

Figure 7:
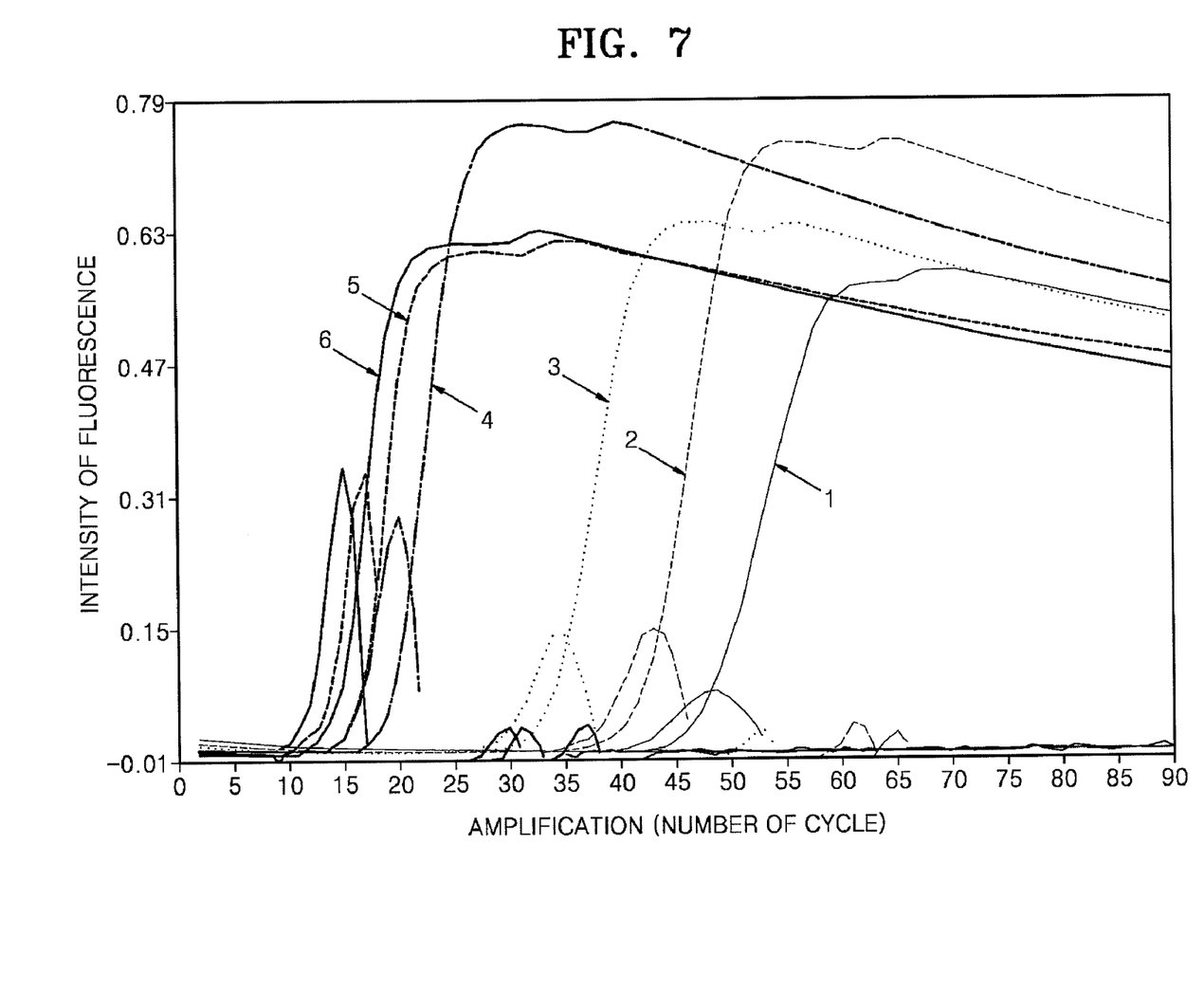
FIG. 7 illustrates results of RCA performed according to the copy number of a nucleic acid, in the presence of a ligase and a restriction enzyme.

FIG. 7 illustrates results of RCA performed according to the copy number of a nucleic acid, in the presence of a ligase and a restriction enzyme. FIG. 7, amplification curves 1-6 were obtained when the copy number of the target nucleic acid was $10^6$, $10^5$, $10^4$, $10^3$, $10^2$, and 10, respectively. Referring to FIG. 7, in a solution containing a ligase and a restriction enzyme, as the copy number of the target nucleic acid decreases, RCA was more slowly performed. Also, high sensitivity was identified in view of amplification at 10 copies. For reference, as for PCR, each step is distinctively distinguished according to a temperature and a Ct value at which amplification is quickly performed can be used to quantify the amount of a template. On the other hand, as for an isothermal reaction, each step cannot be distinguished from each other and thus unlike PCR, kinetics cannot be applied.

While the present invention has been particularly shown and described with reference to exemplary embodiments thereof, it will be understood by those of ordinary skill in the art that various changes in form and details may be made therein without departing from the scope of the present invention as defined by the following claims.

What is claimed is:

1. A method of amplifying a selected nucleic acid molecule, the method comprising subjecting a reaction mixture to rolling circle amplification to perform simultaneously a formation of a single stranded circular DNA molecule which is a copy of the selected nucleic acid molecule and an amplification of the single stranded circular DNA molecule, said reaction mixture comprising
    (a) a first hairpin oligonucleotide which comprises a first loop region, a first double-stranded linear region, and a first single-stranded end sequence ("first overhang sequence"),
    (b) a second hairpin oligonucleotide which comprises a second loop region, a second double stranded linear region, and a second single-stranded end sequence ("second overhang sequence"), wherein the second overhang sequence of the second hairpin oligonucleotide is complementary to the first overhang sequence of the first hairpin oligonucleotide,
    (c) the selected nucleic acid molecule having a single-stranded end sequence complementary to the first or second overhang sequence;
    (d) a DNA ligase capable of ligating the first hairpin oligonucleotide to the second hairpin oligonucleotide and capable of ligating the selected nucleic acid molecule to at least the first or second hairpin oligonucleotide;
    (e) a double-stranded DNA-specific endonuclease capable of cleaving hairpin oligonucleotide dimers at the DNA sequence formed by the ligation of the first hairpin oligonucleotide and the second hairpin nucleotide;
    and the DNA sequence formed at the site of the ligation between the second hairpin oligonucleotide and the selected nucleic acid molecule does not generate a recognition site for the endonuclease of step (e)
    (f) a primer oligonucleotide which is complementary to one or more elements selected from the group consisting of the first hairpin oligonucleotide, the second hairpin oligonucleotide and the selected nucleic acid molecule; and
    (g) a DNA polymerase capable of polymerizing a nucleotide chain extending from the primer oligonucleotide during rolling circle amplification, wherein the single stranded circular DNA molecule is formed by ligating the first hairpin oligonucleotide and the second hairpin oligonucleotide to the selected nucleic acid molecule, and wherein the DNA sequence formed at the site of the ligation between the first hairpin oligonucleotide and the selected nucleic acid molecule does not generate a recognition site for the endonuclease of step (e).

2. The method of claim 1, wherein the primer oligonucleotide is complementary to a contiguous DNA sequence at the site of the ligation between the first or second hairpin oligonucleotide and the selected nucleic acid molecule, wherein the 5' end of the primer is complementary to a DNA sequence within said first or second hairpin oligonucleotide and the 3' end of the primer is complementary to a DNA sequence of said selected nucleic acid molecule.

3. The method of claim 1, wherein the selected nucleic acid molecule is prepared in situ by cleavage of a sample nucleic acid with an endonuclease.

4. The method of claim 3, wherein the selected nucleic acid molecule is prepared in situ by cleavage of a sample nucleic acid with an endonuclease which is the endonuclease of step (e) or differs from the endonuclease of step (e).

5. The method of claim 4, wherein the selected nucleic acid molecule is prepared in situ by cleavage of a sample nucleic acid with an endonuclease which differs from the endonuclease of step (e).

6. The method of claim 1, wherein the first overhang sequence of the first hairpin oligonucleotide and the second overhang sequence of the second hairpin oligonucleotide have a nucleotide sequence which generates a restriction site for the endonuclease of step (e) in a double stranded linear region which is formed by ligation of the first hairpin oligonucleotide and the second hairpin oligonucleotide.

7. The method of claim 1, wherein the selected nucleic acid molecule is double stranded and each strand of the two strands of the selected nucleic acid has a single stranded end sequence at its one end; and wherein the single stranded end sequence of one strand is complementary to the first overhang sequence of the first hairpin oligonucleotide and the single stranded end sequence of the other strand is complementary to the second overhang sequence of the second hairpin oligonucleotide.

8. The method of claim 1, wherein the selected nucleic acid molecule is double stranded and one of the two strands of the selected nucleic acid has a single stranded end sequence at its both ends; and wherein the single stranded end sequence of one end is complementary to the first overhang sequence of the first hairpin oligonucleotide and the single stranded end sequence of the other end is complementary to the second overhang sequence of the second hairpin oligonucleotide.

9. The method of claim 1, wherein the selected nucleic acid molecule is double stranded and has a single stranded end sequence at one end; and wherein the single stranded end sequence of the selected nucleic acid molecule is complementary to one of the first overhang sequence of the first hairpin oligonucleotide or the second overhang sequence of the second hairpin oligonucleotide.

10. The method of claim 1, wherein the selected nucleic acid molecule is ligated, at its one end, to the first hairpin oligonucleotide and, at its other end, to the second hairpin oligonucleotide to form a monomer which has a single-strand hairpin loop at its both ends and has a double stranded linear region.

11. The method of claim 10, wherein the double stranded linear region has or does not have a restriction site for the (e) endonuclease.

12. The method of claim 1, wherein the (d) ligase and the (e) endonuclease is contained in the mixture at a molar ratio of 1:1 by unit.

13. The method of claim 1, wherein the simultaneous formation and amplification of the single stranded circular DNA molecule are performed at a temperature of 4° C. to 80° C.

14. The method of claim 1, wherein the simultaneous formation and amplification of the single stranded circular DNA molecule are performed in a reaction solution containing Mg2+, dNTP, and ATP.

15. The method of claim 2, wherein the single stranded circular DNA molecule is formed in situ from the selected nucleic acid by the action of (e) endonuclease.

16. The method of claim 1, wherein the ligase is selected from the group consisting of Taq DNA ligase, *E. coli* DNA ligase, T4 DNA ligase, and Tfi DNA ligase.

17. The method of claim 1, wherein the (e) endonuclease is selected from the group consisting of type I, II, IIs, Iig, IIb, nicking endonuclease, and McrBC nuclease.

18. The method of claim 1, wherein the (g) DNA polymerase is selected from the group consisting of *E. coli* DNA polymerase I, Klenow fragment, phi29 DNA polymerase, vent DNA polymerase, T4, T7 DNA polymerase, and Taq polymerase.

19. The method of claim 1, wherein said reaction mixture comprises a primer oligonucleotide wherein the DNA sequence of the primer is complementary to the selected nucleic acid molecule.

20. The method of claim 1, wherein the primer oligonucleotide comprises two primer oligonucleotides.

21. The method of claim 1, wherein the selected nucleic acid molecule is prepared in situ by cleavage of a sample nucleic acid with an endonuclease which is selected from the group consisting of type I, II, IIs, Iig, IIb, nicking endonuclease, and McrBC nuclease.

22. The method of claim 1, wherein the DNA sequence formed at the site of the ligation between the first hairpin oligonucleotide and the selected nucleic acid molecule does not generate an endonuclease recognition site and the DNA sequence formed at the site of the ligation between the second hairpin oligonucleotide and the selected nucleic acid molecule does not generate an endonuclease recognition site.

* * * * *